United States Patent [19]

Andrews et al.

[11] Patent Number: 4,741,897
[45] Date of Patent: May 3, 1988

[54] THYROXINE ANALOGS AND REAGENTS FOR THYROID HORMONE ASSAYS

[75] Inventors: Judith Andrews, Wayland; Christine Burns, Wellesley; James Quick, Lexington, all of Mass.

[73] Assignee: Baxter Travenol, Deerfield, Ill.

[21] Appl. No.: 883,241

[22] Filed: Jul. 8, 1986

[51] Int. Cl.$^4$ ............................................. G01N 33/53
[52] U.S. Cl. .......................................... 424/1.1; 435/7;
436/500; 548/335; 548/342; 548/344; 560/12;
560/17; 560/35; 560/40; 562/426; 562/430;
562/440; 562/447; 564/74; 564/157; 564/174;
564/276; 568/33
[58] Field of Search ......................... 424/1.1; 436/500;
435/7; 548/342, 344, 335

[56] References Cited

U.S. PATENT DOCUMENTS 3,983,099  9/1976  Niswender .............................. 560/39
4,225,574  9/1980  Romelli et al. ....................... 436/500
4,489,165  12/1984  Wagner et al. ....................... 436/500

FOREIGN PATENT DOCUMENTS 0026103  4/1981  European Pat. Off. ............ 562/447
WO80/3033-
06       9/1983  PCT Int'l Appl. ................. 436/501

OTHER PUBLICATIONS

J. Stokigt, et al., *Clinical Endocrinology*, 15, 313–318 (1981).

J. Stokigt, et al., *Clinical Chemistry* 29, 1408–1410 (1983).
J. Midgley, et al., *Clinical Endocrinology*, 7, 523–528 (1982).
M. Bayer, *Clinica Chimica Acta*, 130, 391–396 (1983).
N. Amino, et al., *Clinical Chemistry*, 29, 321–325 (1983).
T. Andrea, et al., *Biochemistry*, 19, 55–63 (1980).
W. Wiersinga, et al., in *Methods in Enzymology*, vol. 84, J. Langone, et al., (editors), Academic Press, New York, 1982, pp. 272–302.

*Primary Examiner*—Richard A. Schwartz
*Attorney, Agent, or Firm*—Donald L. Barbeau

[57] ABSTRACT

The present invention relates to new compounds of the general formula:

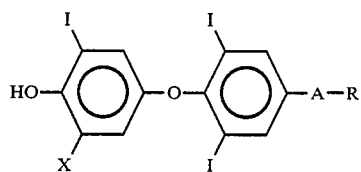

where X is iodine or hydrogen; A is a linking portion; and R is an iodinatable aryl or heteroaryl group having electron donating substituents. These compounds are useful precursors to the iodinated thyroid hormones for radioimmunoassay determination of thyroid hormones in biological fluids.

10 Claims, 1 Drawing Sheet

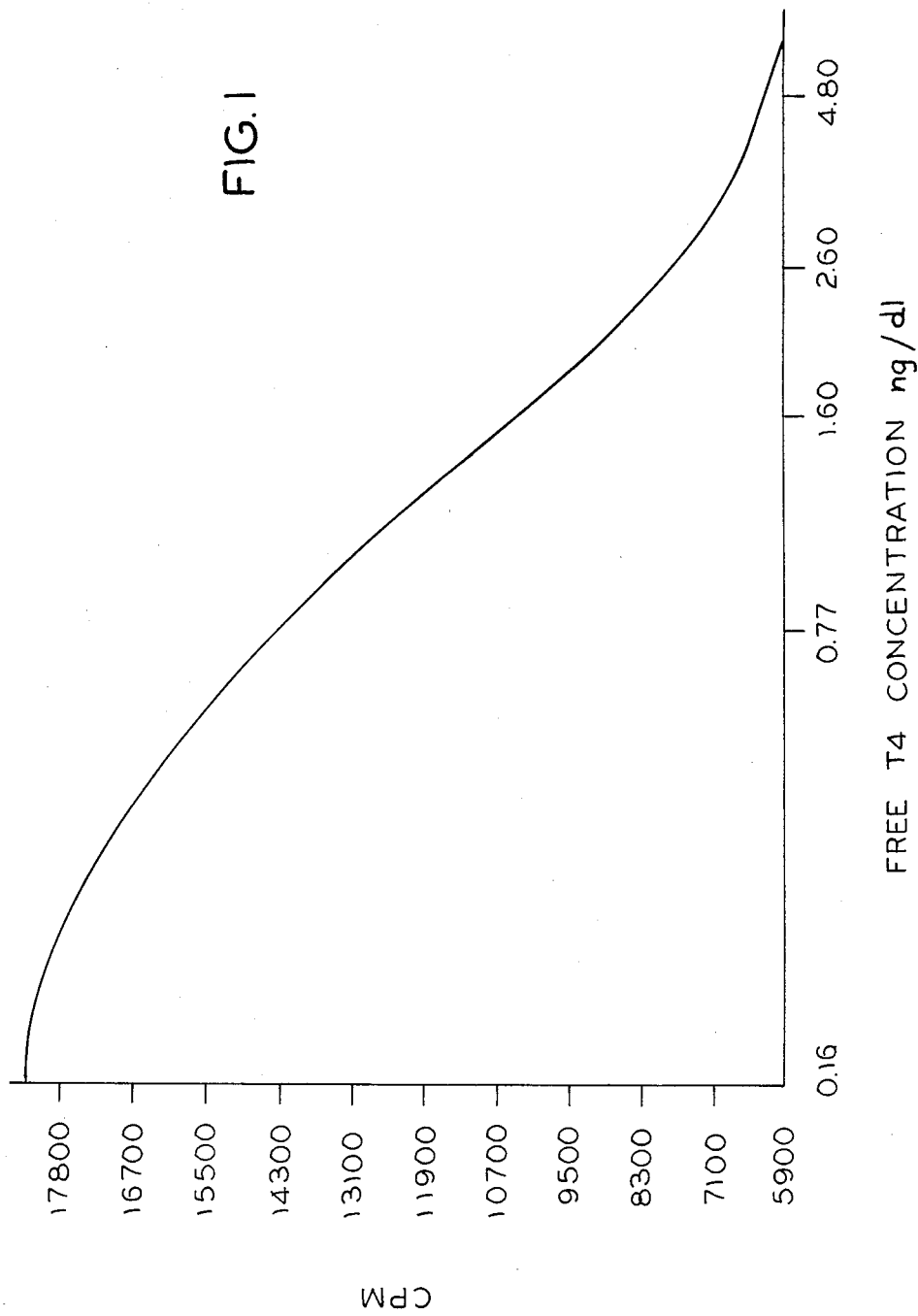

THYROXINE ANALOGS AND REAGENTS FOR THYROID HORMONE ASSAYS

BACKGROUND OF THE INVENTION

The measurement of thyroid hormones in biological fluids has been the object of intense research for a number of years. Proposed methods include determination of bound as well as unbound thyroid hormones. Although the major portion (>99%) of thyroid hormones found in biological fluids are bound to endogenous binding proteins such as thyroxin-binding globulin (TBG) and thyroxin-binding pre-albumin (TBPA) in serum, the determination of free (unbound) thyroid hormones as a measure of thyroid function has attracted the most attention. Considered critically important because of its physiological significance, efforts have been made to estimate the concentration of free thyroxine hormones by a variety of so-called direct and indirect methods using radioimmunoassay (RIA) as the principal measurement system. Nevertheless, attempts to increase the reliability of these free thyroid hormone assays using RIA have been thwarted by the anamolous endogenous protein binding found in metabolic disease states.

The development of analog tracers for the measurement of thyroxine (T4) and triodothyroxine (T3) in serum using competitive immunoassay techniques has been subject of much controversy. (Stockigt, et al. *The Lancet*, Sept. 25, 1982 p. 712; Stockigt, et al. *The New England Journal of Medicine* Vol. 307, p. 126 (1982); Stockigt, et al. *Clinical Endocrinology* Vol. 15, 313–318 (1981); Stockigt, et al. *Clinical Chemistry* 29(7), 1408–1410 (1983); Braun, et al. *Clinical Chemistry* 29(12), 2057–2060 (1983); Midgley et al. *Clinical Endocrinology* Vol. 17, 523–528 (1981); Amino et al. *Clinical Chemistry* 29, 321–325 (1983); and Wilke, *Clinical Chemistry* 32, 585–592 (1986)).

Designed to measure the amount of free T3 or T4 in solution by competitively binding the labelled T3 or T4 analogs to a specific antibody thereto, these assays have been found to give misleading results caused by interaction of thyroxine-binding proteins. In familial dysalbuminemic hyperthyroxinemia for example, an abnormal albumin binds up to 50% of the T4 found in the serum (ca. 12% in normal serum). Because this abnormal albumin binds to the labelled T4 analog to a greater extent than normal albumin, use of the single-step competitive binding procedure would result in less labelled analog being available with binding sites on the T4 antibody. This causes an apparent increase in the free T4 in serum using the one-step procedure.

In patients having severe nonthyroid illness with low levels of T4 and serum prealbumin, the labelled analog does not bind to proteins as well as in normal serum. This causes an apparent decrease in the free T4 in serum.

Heretofore, methods for measuring free thyroxine hormones in biological fluids using labelled thyroxine analogs have relied on the assumption that the level of antibody-binding of a tracer that does not bind to plasma proteins varies inversely with the concentration of free thyroxine in solution. Commercially available thyroxine analogs have not proven satisfactory tracers in immunoassay because of significant amounts of residual (anamolous) binding to plasma proteins such as thyroxine-binding globulins and albumin.

In accordance with the present invention, we have found thyroxine analogs useful for RIA of thyroxine and triiodothyroxine having a reduced tendency to interact with thyroxine-binding globulin in biological fluids. These new thyroxine analogs are particularly advantageous in measuring thyroxine concentrations in patients having abnormal plasma protein conditions. Moreover, these new analogs are easily iodinatable and controlled giving a high specific activity.

SUMMARY OF THE INVENTION

The present invention relates to compound of the formula:

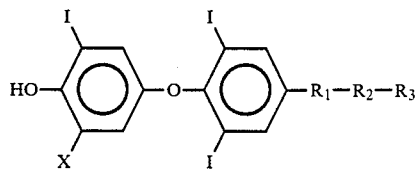

where X is iodine or hydrogen; $R_1$ is

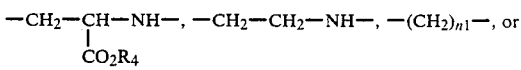

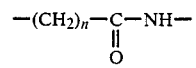

where $n_1$ is from 0 to about 4, n is from 0 to about 5, and $R_4$ is hydrogen, methyl, ethyl, or propyl; $R_2$ is a bifunctional linking compound; and $R_3$ is

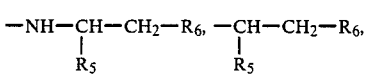

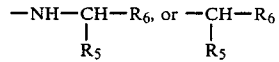

where $R_5$ is hydrogen, $-CO_2R_4$ or $-NH_2$ and $R_6$ is

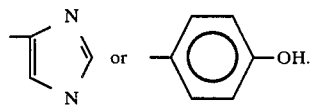

These compounds are useful precursors for the preparation of radioactive labelled components of immunoassays for the determination of thyroxine or triiodothyroxine in biological fluids.

DETAILED DESCRIPTION OF THE PREFERRED EMBODIMENT OF THE INVENTION

In accordance with the present invention, compounds having the formula:

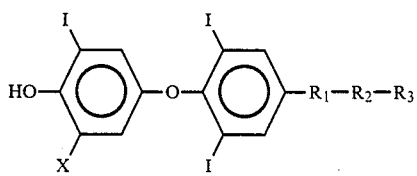

are described. These compounds have been found particularly useful as iodinatable thyroxine analogs in the direct determination of thyroxine and triiodothyroxine in biological fluids such as serum. We have unexpectedly found that compounds in accordance with the present invention have minimal interactions with thyroxin-binding globulin in biological fluids. Preferred compounds in accordance with the present invention have been found not to bind significantly to this serum protein.

In accordance with the present invention, $R_1$ may be

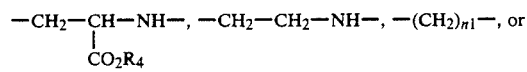

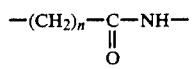

where $R_4$ is hydrogen, or a lower alkyl having from about 1 to about 3 carbon atoms such as methyl, ethyl or propyl; $n_1$ is from 0 to about 4 and n is from 0 to about 5. In accordance with a preferred embodiment of the present invention, $n_1$ is 1 or 2.

In accordance with the present invention, $R_2$ may be a direct bond, or a bifunctional linking group having the preferred formula

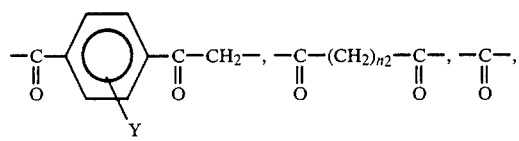

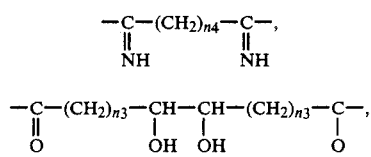

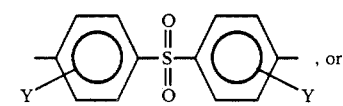

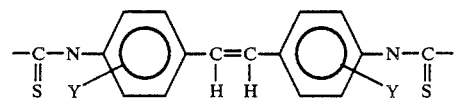

where $n_2$ is from about 2 to about 6, $n_3$ is from about 0 to about 2, $n_4$ is from about 4 to about 6, and Y is hydrogen, $-OR_4$, or $NO_2$.

In accordance with the present invention, $R_3$ may be

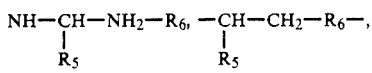

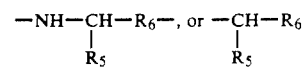

where $R_5$ is hydrogen, $-CO_2R_4$ or $-NH_2$.

In accordance with the present invention, $R_6$ is a ready iodinatable aryl or heteroaryl group having electron donating substituents such as

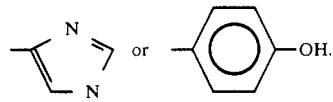

The following examples are provided to illustrate the present invention and are not intended to limit the scope thereof.

EXAMPLE 1

N-Imidazylethyl 3,3',5,5'-tetraiodothyroacetamide

This example describes the synthesis of a compound having the formula:

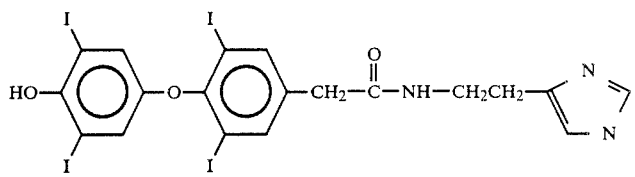

A mixture of 15 mg 3,3',5,5'-tetraiodothyroacetic acid in methanol/water and 4.4 mg solid 1-ethyl-3(3-dimethylaminopropyl)carbodimide-HCL was stirred for one hour at room temperature. The free base of histamine (2.73 mg) was dissolved in water and added to the resulting mixture and stirred for an additional hour prior to purification by HPLC on a Hamilton Semi-Preparative PRP-1 column of styrene and divinylbenzene (30% 0.005M PICB-7 buffer gradient in acetonitrile).

EXAMPLE 2

N-imidazylethyl 3,3',5-triiodothyropropionamide

This example describes the synthesis of a compound having the formula:

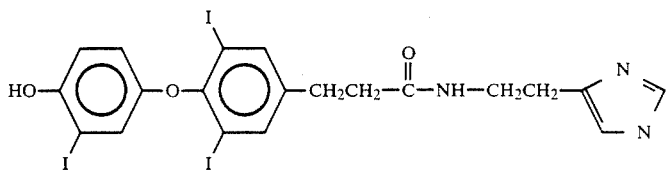

The compound was prepared and purified as in Example 1 in all essentional details with the exception that an equivalent amount of 3,3',5-triiodothyropropionic acid was substituted for 3,3',5,5'-tetraiodothyroacetic acid.

EXAMPLE 3

N-p-hydroxylphenylethyl 3,3',5 triiodothyropropionamide

This example describes the synthesis of a compound having the formula:

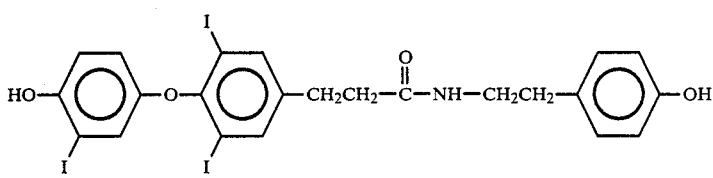

The compound was made and purified as in Example 2 in all essential details with the exception that an equivalent amount of tyramine was substituted for histamine.

EXAMPLE 4

L-thyroxine-histamine supramide

This example describes the synthesis of a compound having the formula:

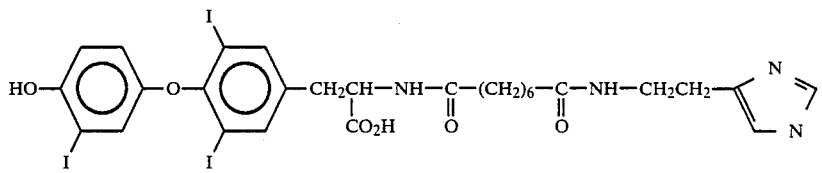

A mixture of 4.94 g of L-thyroxine (sodium salt) and 0.65 g histamine (free base) in 400 ml deionized water and 800 ml acetonitrile was stirred in the dark until dissolved. To this solution, 2.1 g of disuccimidyl suberate (DSS) in 45 ml acetonitrile was added by a dropping funnel. The resulting mixture was stirred overnight at room temperature and then stored at 4° C. until purification. A white precipitate was collected by centrifugation and decantation of the mixture described above after concentration to 20% of its original volume in vacuo at a temperature less than 30° C.

The white precipitate was dissolved in DMSO and purified by HPLC on a Hamilton PRP-1 preparative column using a gradient of from 80% PIC-B7 (waters) to 60% Acetonitrile. The mass spectra analysis was consistent with the assigned structure.

EXAMPLE 5

L-triiodothyroxine-histamine supramide

This example describes the synthesis of a compound having the formula:

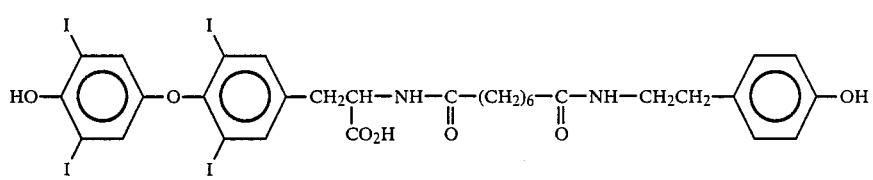

The compound was made and purified as in Example 4 in all essential details with the exception that an equivalent amount of triiodothyroxine was substituted for thyroxine. The mass sepctra analysis was consistent with the assinged structure.

EXAMPLE 6

L-thyroxine-tyramine supramide

This example describes the synthesis of a compound having the formula:

The compound was made and purified as in Example 4 in all essential details with the exception that an equivalent amount of tyramine was substituted for histamine.

EXAMPLE 7

L-triiodothyroxine-tyramine supramide

This example describes the synthesis of a compound having the formula:

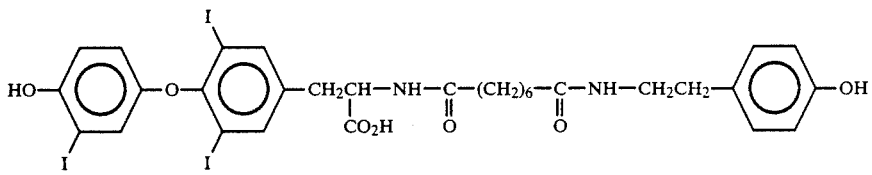

The compound was made and purified as in Example 4 in all essential details with the exception that equivalent amounts of tyramine and triiodothyroxine were substituted for histamine and thyroxine respectively.

EXAMPLE 8

This example describes the iodination of the compound prepared in Example 4 to one having the formula:

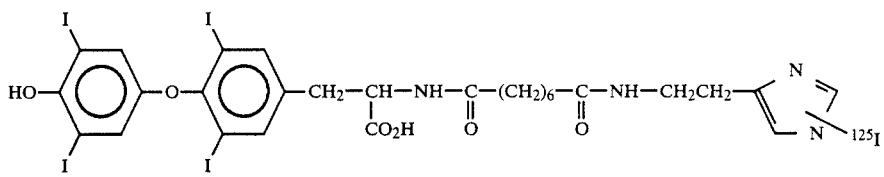

A quantity of 400 ug of T4-DSS-Histamine in 0.05 ml DMSO and 0.05 ml H$_2$O was mixed with 35 mCi sodium iodide (carrier free) and 0.44 mg Chloramine T in 0.3 ml of a 0.5M sodium phosphate buffer at pH 7.0 for three minutes. The reaction was terminated with 0.68 mg of sodium meta bisulfate in 0.5M sodium phosphate at pH 7.0. The mixture was then applied to a C-18 reverse-phase HPLC column and eluted with a linear gradient of 0 to 60% methanol in H$_2$O. Unbound iodide eluted in the column void volume and the iodinated T4-DSS-Histamine eluted as a single peak at approximately 50% methanol.

EXAMPLE 9

This example describes the use of an iodinated compound having the formula (prepared as in Example (8):

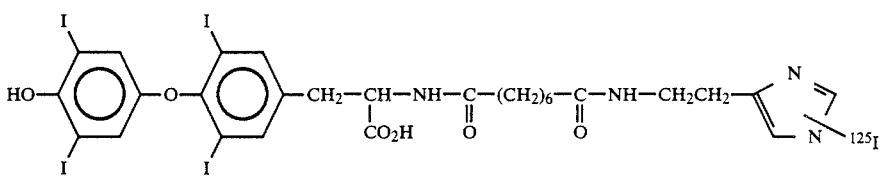

in an immunoassay for the direct determination of free (unbound) thyroid hormones.

To each of nine duplicate GAMMACOAT ™ (Clinical Assays, Cambridge Massachusetts) tubes coated on its inside wall with rabbit anti-T4 antibody, was added a known amount of free L-thyroxine. To each of tubes 1 through 6 was added 50 ul of thyroxine standards having from 0.00 to 4.80 ng/dl thyroxine respectively as shown in TABLE 1; and to each of tubes 7 through 9 was added 50 ul of control serum containing a known amount of thyroxine as shown in TABLE 2.

To each of the tubes was added 1.0 ml of the iodinated tracer compound made in accordance with Example 8 in Tris-buffered saline and having a (specific) activity of 0.7 uCi/ml. The resulting mixture was incubated for 90 minutes at 37° C. and the (supernatant) decanted. The tubes were then counted in a gamma counter for one minute with the window adjusted for iodine-125. The results for the thyroxine standards of tubes 1 through 6 are shown in TABLE 1:

TABLE I

| TUBE | FREE T4 STANDARD | MEAN CPM | % B/B$_0$ |
|---|---|---|---|
| 1 | 0.00 ng/dl | 21919 | — |
| 2 | 0.16 ng/dl | 18538 | 84.6 |
| 3 | 0.77 ng/dl | 14703 | 67.1 |
| 4 | 1.60 ng/dl | 10662 | 48.6 |
| 5 | 2.60 ng/dl | 8587 | 39.2 |
| 6 | 4.80 ng/dl | 6043 | 27.6 |

A standard curve was prepared from the thyroxine standards so that the unknown thyroxine values could be determined by interpolation of the curve. The standard curve is shown in FIG. 1. The concentration of free thyroxine in the three control sera was determined from the standard curve depicted in FIG. 1. The results for the thyroxine concentration in the control sera of tubes 7 through 9 are shown in TABLE 2:

TABLE 2

| TUBE | FREE T4 IN CONTROL SERUM | MEAN CPM | FREE T4 CONCENTRATION |
|---|---|---|---|
| 7 | 0.74 ng/dl ±.18 | 15532 | 0.62 ng/dl |
| 8 | 1.72 ng/dl ±.20 | 10888 | 1.59 ng/dl |
| 9 | 3.56 ng/dl ±.38 | 7697 | 3.24 ng/dl |

The present invention has been described in detail and with particular reference to the preferred embodiments; however, it will be understood by one having ordinary skill in the art that changes can be made thereto without departing from the spirit and scope thereof.

We claim:

1. A compound of the formula:

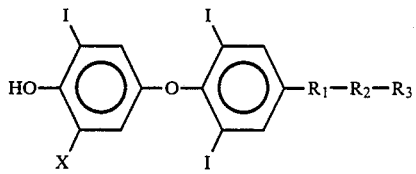

wherein
X is iodine or hydrogen;
R₁ is

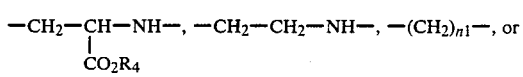

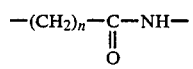

where $n_1$ is an integer from 0 to about 4, n is an integer from 0 to about 5, and R₄ is hydrogen, methyl, ethyl, or propyl;
R₂ is

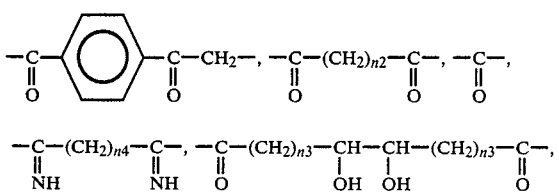

where $n_2$ is an integer from about 2 to about 6, $n_3$ is an integer from about 0 to about 2, and $n_4$ is an integer from about 4 to about 6; and
R₃ is

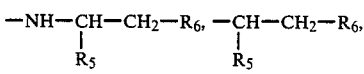

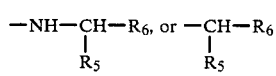

where R₅ is hydrogen, CO₂R₄ or —NH₂ and R₆ is

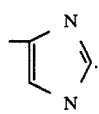

2. The compound of claim 1 wherein R₁ is

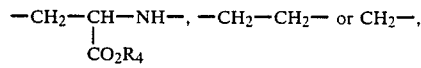

R₂ is

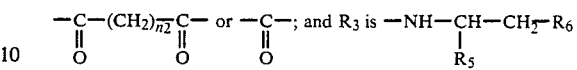

where R₅ is —CO₂R₄ or hydrogen.

3. The compound of claim 2 wherein R₂ is

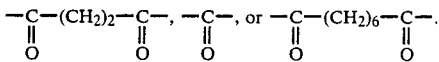

4. The compound of claim 2 wherein R₁ is —CH₂—CH₂ and R₂ is

5. The compound of claim 4 wherein R₃ is —NH—CH₂—CH₂—R₆.

6. A reagent for determining thyroxine or triiodothyroxine in a biological fluid, said reagent comprising an antibody capable of immunologically reacting with said thyroxine or triiodothyroxine and a labelled ligand capable of binding to said antibody, said labelled ligand having the formula

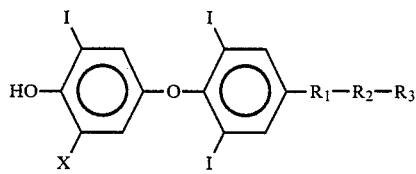

wherein
X is iodine or hydrogen;
R₁ is

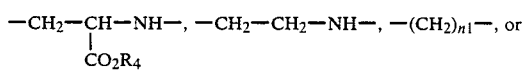

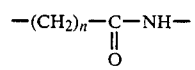

where $n_1$ an integer from 0 to about 4, n is an integer from 0 to about 5, and R₄ is hydrogen, methyl, ethyl, or propyl;
R₂ is

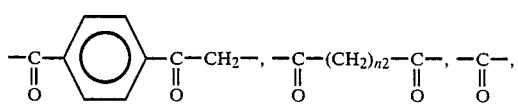

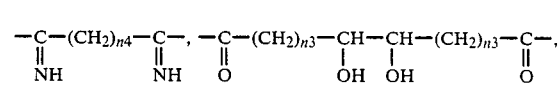

-continued

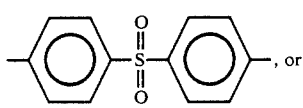, or

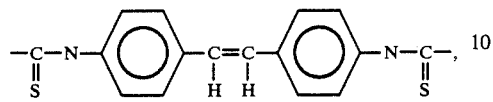

where $n_2$ is an integer from about 2 to about 6, $n_3$ is an integer from about 0 to about 2, and $n_4$ is an integer from about 4 to about 6; and $R_3$ is

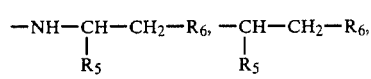

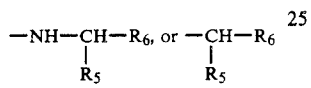

where $R_5$ is hydrogen, $CO_2R_4$ or $-NH_2$ and $R_6$ is

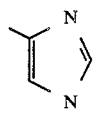

wherein $R_6$ is labelled with radioactive iodine.

7. The reagent of claim 6 wherein $R_6$ is

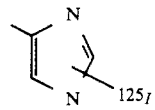

8. The reagent of claim 7 wherein $R_1$ is

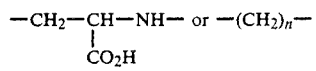

where n is 1 or 2;
$R_2$ is

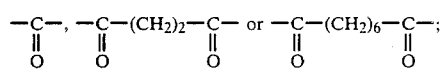

and $R_3$ is $-NHCH_2CH_2-R_6$.

9. The reagent of claim 8 wherein $R_1$ is $-CH_2-CH_2-$; and $R_2$ is

10. The reagent of claim 8 wherein $R_1$ is

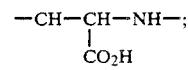

and
$R_2$ is

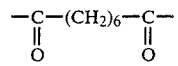

* * * * *

UNITED STATES PATENT AND TRADEMARK OFFICE
CERTIFICATE OF CORRECTION

PATENT NO. : 4,741,897

DATED : May 3, 1988

INVENTOR(S) : Judith Andrews, et al

It is certified that error appears in the above-identified patent and that said Letters Patent is hereby corrected as shown below:

On the title page, item [73] should be corrected to read:

--Baxter Travenol Laboratories, Inc.--.

Signed and Sealed this

Thirteenth Day of December, 1988

Attest:

DONALD J. QUIGG

*Attesting Officer*  *Commissioner of Patents and Trademarks*